United States Patent
Skogö et al.

(10) Patent No.: US 8,066,375 B2
(45) Date of Patent: Nov. 29, 2011

(54) EYE TRACKER HAVING AN EXTENDED SPAN OF OPERATING DISTANCES

(75) Inventors: Mårten Skogö, Bromma (SE); John Elvesjö, Stockholm (SE); Bengt Rehnström, Västerhaninge (SE)

(73) Assignee: Tobii Technology AB, Danderyd (SE)

( * ) Notice: Subject to any disclaimer, the term of this patent is extended or adjusted under 35 U.S.C. 154(b) by 567 days.

(21) Appl. No.: 12/089,595

(22) PCT Filed: Aug. 28, 2006

(86) PCT No.: PCT/SE2006/050296
§ 371 (c)(1),
(2), (4) Date: Aug. 5, 2008

(87) PCT Pub. No.: WO2007/043954
PCT Pub. Date: Apr. 19, 2007

(65) Prior Publication Data
US 2008/0284980 A1    Nov. 20, 2008

Related U.S. Application Data

(60) Provisional application No. 60/726,065, filed on Oct. 12, 2005.

(30) Foreign Application Priority Data

Oct. 10, 2005  (SE) ...................... 0502228

(51) Int. Cl.
    *A61B 3/14*    (2006.01)

(52) U.S. Cl. ...................................... 351/209

(58) Field of Classification Search .......... 351/209–210; 235/454, 462.45, 459
See application file for complete search history.

(56) References Cited

U.S. PATENT DOCUMENTS 5,748,371 A    5/1998   Cathey, Jr. et al.
(Continued)

FOREIGN PATENT DOCUMENTS

EP    1336372 A2    8/2003
(Continued)

OTHER PUBLICATIONS

Database WPI; Week 199844, Derwent Publications Ltd, London, GB; Class P31, AN 1998-510117 & JP10221016-A (NIDE) NEC Corp, Aug. 21, 1998.
Morimoto, C.H. et al; Detecting Eye Position and Gaze from a Single Camera and 2 Light Sources. Proceedings of 16th International Conference on Pattern Recognition, 2002, IEEE Comput. Soc, Los Amlamitos, CA, USA, vol. 4, pag. 314-317, ISBN 0-7695-1695-X.
(Continued)

*Primary Examiner* — Scott J Sugarman
*Assistant Examiner* — Mahidere Sahle
(74) *Attorney, Agent, or Firm* — Moore & Van Allen PLLC; W. Kevin Ransom

(57) ABSTRACT

The present invention relates to automatic registration and tracking of the eyes of at least one subject. An optical system, including a lens structure, a mask and an image sensor, receives incoming light from a scene containing the subject and directs at least a portion of this light towards the image sensor, which registers spatially distributed light and thus produces primary data. The mask is to alter a basic optical transfer function of the lens structure and the image sensor into an enhanced optical transfer function, which is substantially less sensitive to variations of an unknown distance between the optical system and the subject than the basic optical transfer function. The processing unit is to receive the primary data and process this data to produce resulting eye-tracking data representing a position estimate of the at least one eye and/or a gaze direction for the at least one eye.

24 Claims, 3 Drawing Sheets

U.S. PATENT DOCUMENTS

| | | |
|---|---|---|
| 5,963,300 A | 10/1999 | Horwitz |
| 6,152,371 A | 11/2000 | Schwartz et al. |
| 2004/0005083 A1 | 1/2004 | Fujimura et al. |
| 2005/0100191 A1 | 5/2005 | Harbach et al. |
| 2005/0119642 A1 | 6/2005 | Grecu et al. |
| 2006/0238707 A1* | 10/2006 | Elvesjo et al. ............ 351/209 |
| 2009/0067680 A1* | 3/2009 | Dowski et al. ............ 382/115 |

FOREIGN PATENT DOCUMENTS

| | | |
|---|---|---|
| JP | 6082680 A | 3/1994 |
| JP | 9211310 A | 8/1997 |
| JP | 2000137792 A | 5/2000 |
| WO | 2004045399 A1 | 6/2004 |
| WO | 2004090581 A2 | 10/2004 |

OTHER PUBLICATIONS

Yoshinobu Ebisawa: "Improved Video-Based-Eye-Gaze Detection Method", Conference 10th Anniversary, IMTc/94, Advanced Technologies in I & M, 1994 IEEE Instrumentation and Measurement Technology Conference, New York, NY, USA, vol. 2, pag. 963-966, ISBN 0-7803-188-3.

International Preliminary Report on Patentability.

International Search Report.

Japanese Office Action for JP Application 2008-534493, dated Oct. 22, 2010.

* cited by examiner

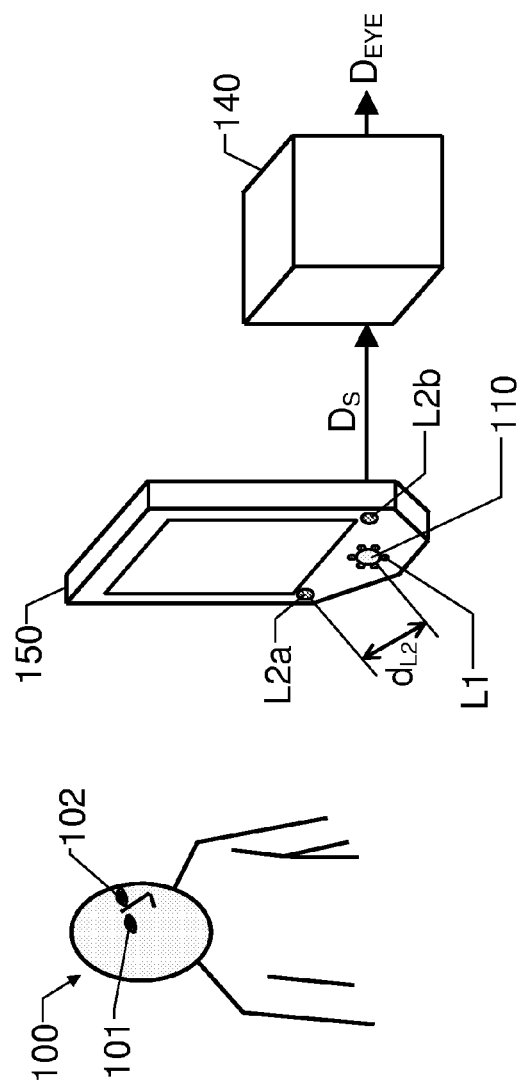
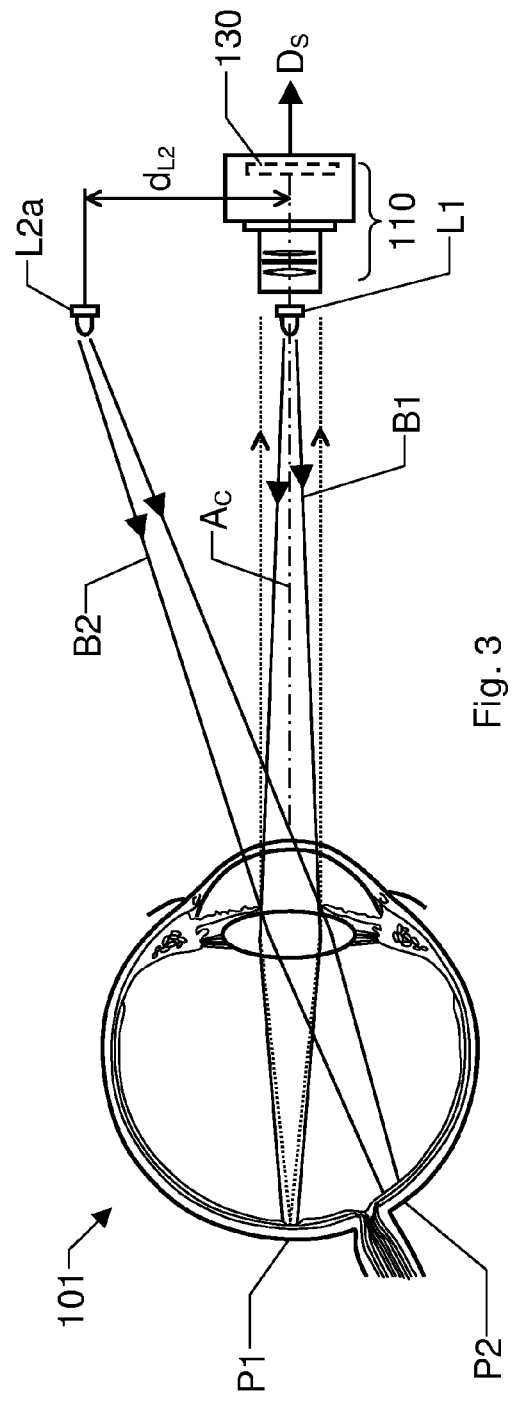
Fig. 2
Fig. 3

EYE TRACKER HAVING AN EXTENDED SPAN OF OPERATING DISTANCES

CROSS REFERENCE TO RELATED APPLICATIONS

The present application claims priority to U.S. Provisional Patent Application Ser. No. 60/726,065 titled "Eye Tracker Having an Extended Span of Operating Distances" filed on Oct. 12, 2005.

THE BACKGROUND OF THE INVENTION AND PRIOR ART

The present invention relates generally to automatic eye tracking wherein the tracking precision is enhanced based on an optical-transfer-function modifying mask, which enables the eye tracker to work within a relatively large range of distances. More particularly the invention relates to a system according to the preamble of claim 1 and a method according to claim 14. The invention also relates to a computer program according to claim 23 and a computer readable medium according to claim 24.

The concept of eye tracking is well known in the art, and a number of different techniques have been developed for accomplishing automatic eye and gaze tracking. In the area of remote, non-obtrusive eye tracking, the most commonly used designs are based on pupil center corneal reflection (PCCR) methods. The basic idea behind this approach is to use at least one light source, and by means of a camera, capture a series of images of the eye. In each image the light source's reflection, the glint, in the cornea and the pupil are identified. A vector defined from the glint to the center of the pupil is then used to estimate the eye's gaze direction. Furthermore, within the PCCR-eye-tracking field there exist two main strategies to identify the pupil in the above-mentioned images. The light source may be positioned as close as possible to the camera's optical axis. This results in that a part of the eye's retina illuminated by the light source reflects light back into the camera, and hence the pupil appears bright in the registered images. Tracking solutions based on this strategy are therefore categorized as bright-pupil (BP) PCCR. Alternatively, the light source can be positioned at a distance from the camera's optical axis. As a result, essentially no light from the light source will be reflected via the retina into the camera, and the pupil appears dark in the registered images. Tracking solutions based on this strategy are therefore categorized as dark-pupil (DP) PCCR.

Whether BP- or DP-PCCR is preferable depends on i.a. the ambient light conditions, the subject's age and gender because these factors influence the pupil area. Moreover, the BP response is highly influenced by the ethnicity of the person whose eyes are being tracked. For instance, it has been found that Hispanics generally have a very strong BP response and Caucasians have a somewhat weaker BP response, however still fair enough. Nevertheless, Asians in many cases have an in adequate BP response. Hence, in order to ensure a reliable eye tracking, a combination of BP- and DP-PCCR tracking is often desirable.

The published International Patent Application WO 2004/045399 describes a system wherein the eyes' positions and gaze directions are detected and tracked. The system includes a camera and a number of light sources, which are distributed around a display, e.g. a computer screen. By sequentially illuminating a subject viewing the display with light from different light sources it is possible to alternatively detect the eyes' position and the gaze direction. However, in order to perform this evaluation, the camera must generate data of high image quality. This, in turn, requires high-class optics, a high-performance image sensor and/or well-controlled light conditions. It is also very important that the subject's eyes remain in focus during the tracking procedure. To this aim, the camera must either be equipped with an auto-focus arrangement, or operate with an optical system that has a comparatively small numerical aperture (i.e. a high F-number) to accomplish a sufficiently large depth of field. The former alternative renders the camera complex, heavy and expensive, while the latter alternative further increases the performance requirements on the image sensor, which is a parameter that also translates into cost.

The U.S. Pat. No. 5,748,371 discloses a system for increasing the depth of field and decreasing the wavelength sensitivity and the misfocus-producing aberrations of the lens of an incoherent optical system. This technique is referred to as wavefront coding. Here, a special purpose optical mask is included in the incoherent optical system. The mask alters the optical transfer function, such that it remains essentially constant within some range from the in-focus position of the unaltered system. Signal processing of a resulting intermediate image undoes the optical transfer modifying effects of the mask, which provides an in-focus image over an increased depth of field. Although this system is efficient in terms of enabling a long focus range based on relatively simple and low-cost optics and sensors, the design is not well suited for direct implementation in an automatic eye tracking system. Namely, here, eye-tracking specific image parameters, such as eye positions and gaze directions, must be derivable with very high accuracy, whereas essentially all other image data may be discarded. For example, when a rough estimation of the eyes' position has been made the eye-tracking camera normally zooms in (optically, or digitally) towards this position, and/or selects a so-called region of interest (ROI) on the image sensor around this position, to improve the gaze tracking precision and/or reduce the data rate to the image processor. Nevertheless today, there is no wavefront-coding based design, which is adapted to enable any operations of this kind.

SUMMARY OF THE INVENTION

The object of the present invention is therefore to provide a robust and cost-efficient solution, which alleviates the above problems and thus enables a reliable automatic eye tracking over a relatively long range of distances to the user, and which also allows comparatively large variations in the ambient light conditions.

According to one aspect of the invention, the object is achieved by the system as initially described, wherein the optical system further includes a mask, which is arranged between the at least one subject and the image sensor. The mask is adapted to alter the basic optical transfer function into an enhanced optical transfer function, which is adapted to spread an image from one point in space onto more than one sensor element on a sensor surface of the image sensor. The enhanced optical transfer function is also substantially less sensitive to variations of an unknown distance between the optical system and the at least one subject than the basic optical transfer function. Moreover, the processing unit is adapted to receive the primary data and process this data to produce resulting eye-tracking data, which in turn, represents a position estimate of the at least one eye and/or a gaze direction for the at least one eye.

Important advantages of this system are that the image sensor can be made relatively simple. The system is also relatively robust with respect to noise in the data registered by the image sensor. Furthermore, the quality requirements on the lens structure may be comparatively low, which vouches for low cost, According to one preferred embodiment of this aspect of the invention, the image sensor is adapted to exclusively transfer a high-relevance fraction of the primary data to the processing unit. The processing unit, in turn, is adapted to select the high-relevance fraction based on previously derived eye-tracking data and/or data registered by one or more auxiliary sensors connected to the system. Hence, the processing unit's resources can be used more efficiently.

According to another preferred embodiment of this aspect of the invention, the enhanced optical transfer function is adapted to project light reflected from a single point in the scene onto a number of sensor elements of a sensor surface in the image sensor. Thereby, a resolution level is emulated which is higher than a basic resolution level given by the basic optical transfer function and a physical sensor element density of the sensor surface. Furthermore, the processing unit is adapted to process the primary data, such that the eye-tracking data is derived at a precision being superior to a maximum precision attainable exclusively based on eye-tracking data derived from primary data at the basic resolution level of a classic in-focus system. Naturally, this is a very desirable enhancement of the data quality. For example, the result of any digital zooming operations with respect to the eye-tracking data is improved. Moreover, the negative influence of any defective sensor elements on the image sensor may be reduced considerably.

According to yet another preferred embodiment of this aspect of the invention, the processing unit is adapted to match the primary data against a target shape representing a typical eye shape transformed by the optical transfer function. Thereby, eye candidates may be detected efficiently in the scene.

According to still another preferred embodiment of this aspect of the invention, the processing unit is adapted to select a fraction of the primary data that represents a respective region of interest on the sensor surface around each set of sensor elements that has a correlation with the target shape above a match threshold level. Hence, only image data which represents potentially interesting information is delivered to the processing unit for further processing. Of course, this is efficient regarding the utilization of the processing unit's processing capacity.

According to another preferred embodiment of this aspect of the invention, the processing unit is adapted to determine positions of elements in the scene which represent eye candidates, i.e. preliminary eye positions. Then, after having determined a set of position candidates, the processing unit is adapted to match data sub-sets of the primary data representing each of the position candidates against an eye model representing an ideal eye shape transformed by the optical transfer function to obtain a set of correlation test values. Subsequently, based on the correlation test values, the processing unit is adapted to select, at least one position candidate from the set of position candidates to represent at least one eye. Preferably, the processing unit here selects position candidates having correlation test values above a threshold level. Hence, the user's eyes can be identified quickly, such that the tracking may be initiated thereafter.

According to another preferred embodiment of this aspect of the invention, the system includes at least one first and at least one second light source. The at least one first light source is arranged relatively proximate to an optical axis of the optical system, and is oriented such that a main light beam emitted from the light source essentially coincides with the optical axis. The light energy from the at least one first light source is predominantly distributed within a first wavelength range. The at least one second light source is adapted to emit light predominantly within a second wavelength range, essentially separated from the first wavelength range, towards the at least one subject. The at least one second light source is arranged at a distance from the optical axis of the imaging device, such that a main light beam emitted there from is positioned off-axis with respect to this optical axis. Consequently, the at least one first light source creates a bright-pupil effect and the at least one second light source creates a dark-pupil effect.

According to yet another preferred embodiment of this aspect of the invention, the mask is adapted to realize a first optical transfer function with respect to light within the first wavelength range, and direct light within this range to a first area on a sensor surface of the image sensor. The mask is also adapted to realize a second optical transfer function with respect to light within the second wavelength range, and direct light within this range to a second area on the sensor surface. The processing unit is adapted to produce a bright-pupil eye-tracking parameter based on a first sub-set of the primary data registered by sensor elements within the first area, and/or correspondingly produce a dark-pupil eye-tracking parameter based on a second sub-set of the primary data registered by sensor elements within the second area. Thus, the subject can be constantly illuminated by means of both the first and second light sources while the processing unit derives the bright- and dark-pupil eye-tracking parameters in parallel. This provides a high tracking quality under wide ranges of circumstances and conditions.

According to still another preferred embodiment of this aspect of the invention, the image sensor instead includes a first and a second set of sensor elements. Each element in the first set is adapted to detect light within the first wavelength range, and each element in the second set is adapted to detect light within the second wavelength range. Analogous to the above, the processing unit is here adapted to produce a bright-pupil eye-tracking parameter based on a first sub-set of the primary data registered by the first set of sensor elements, and produce a dark-pupil eye-tracking parameter based on a second sub-set of the primary data registered by the second set of sensor elements. Also in this case, the subject can be constantly illuminated by means of both the first and second light sources while the bright- and dark-pupil eye-tracking parameter are derived in parallel. Preferably, each element in the first set of sensor elements adjoins at least one element in the second set of sensor elements. For example, the elements in the first and second sets of sensor elements may be arranged in a checkered pattern. The resolution lost in the primary data by this configuration can be compensated for to some extent in the eye-tracking data by means of the above-described transform function, which is adapted to produce data at an increased image resolution level.

Specifically, according to one preferred embodiment of this aspect of the invention, the enhanced optical transfer function is adapted to project light reflected from a single point in the scene onto a number of the elements in the first and second sets of sensor elements. Thereby, emulation of a resolution level is rendered possible, which is higher than a basic resolution level given by the basic optical transfer function and a physical sensor element density of the sensor surface. The processing unit is adapted to process the primary data, such that the eye-tracking data is derived at a precision being superior to a maximum precision attainable exclusively based on eye-tracking data derived from primary data at the basic resolution level of a classic in-focus optical system.

According to another preferred embodiment of this aspect of the invention, the processing unit is adapted to produce the eye-tracking data based on the bright- and/or the dark-pupil eye-tracking parameters, for example via an intermediate composite representation. Again, this vouches for robustness and a high tracking quality under wide ranges of circumstances and conditions.

According to a further aspect of the invention the object is achieved by a method of automatically registering and tracking at least one eye of at least one subject. It is here presumed that primary data is registered, which represents spatially distributed light. It is further presumed that the light has been transmitted from a scene containing the at least one subject via an optical system, including a lens structure and a mask, to an image sensor, where the primary data is registered. The mask is adapted to alter a basic optical transfer function of the lens structure and the image sensor into an enhanced optical transfer function, which is substantially less sensitive to variations of an unknown distance between the optical system and the at least one subject than the basic optical transfer function. The method involves receiving the primary data, and processing the primary data to produce resulting eye-tracking data, which represents a position estimate of the at least one eye and/or a gaze direction for the at least one eye The advantages of this method, as well as the preferred embodiments thereof, are apparent from the discussion hereinabove with reference to the proposed system.

According to yet a further aspect of the invention the object is achieved by a computer program, which is directly loadable into the internal memory of a computer, and includes software for controlling the above proposed method when said program is run on a computer.

According to another aspect of the invention the object is achieved by a computer readable medium, having a program recorded thereon, where the program is to control a computer to perform the above-proposed method.

The invention is suitable for all kinds of eye-tracking applications, i.e. for controlling computers and computer programs, within psychology and vision research, usability and advertisement evaluations, e.g. so-called attention sensors in warehouse windows. The invention also has medical application in the diagnosis of various eye decreases and Alzheimer's decease, as well as when performing laser eye surgery. Additionally, the invention may be used in auto stereoscopic displays, simulators, and various automotive and avionics applications.

Further advantages, advantageous features and applications of the present invention will be apparent from the following description and the dependent claims.

BRIEF DESCRIPTION OF THE DRAWINGS

The present invention is now to be explained more closely by means of preferred embodiments, which are disclosed as examples, and with reference to the attached drawings.

FIG. 2 shows an overview of a system according to one embodiment of the invention;

FIG. 3 illustrates further details of a lightning and imaging device arrangement according to one embodiment of the invention;

DESCRIPTION OF PREFERRED EMBODIMENTS OF THE INVENTION

Figure 1:
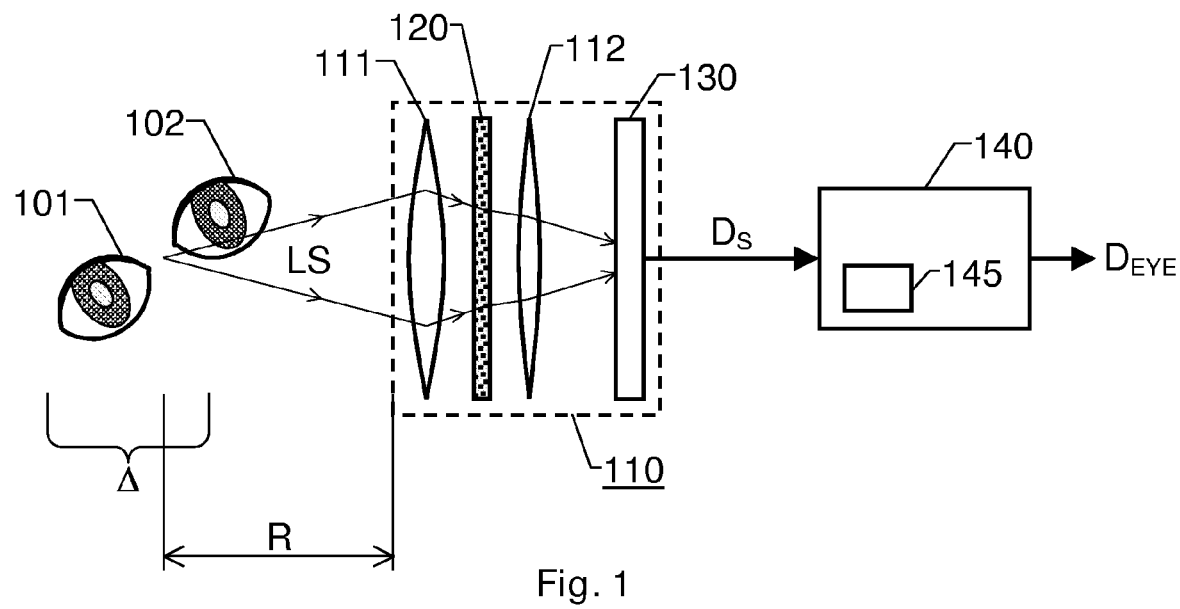
FIG. 1 shows a schematic picture of an eye-tracking system according to the invention.

We refer initially to FIG. 1, which shows a schematic picture of an eye-tracking system according to the invention for automatically registering and tracking at least one eye 101 and 102 of at least one subject, e.g. a user of a computer system. The eye-tracking system includes an optical system 110 and a processing unit 140.

The optical system 110 is adapted to receive and register incoming light reflected from a scene containing the at least one subject 100. To this aim, the system 110 includes an image sensor 130, which is adapted to register primary data $D_s$ represented by spatially distributed light.

The optical system 110 also includes a lens structure, here represented by a schematic pair of lenses 111 and 112, and a mask 120. According to the invention, the specific order of the lens structure 111; 112 and the mask 120 may be varied. For example, the mask 120 may be located in front of, or behind, the entire lens structure 111; 112, or as shown in the FIG. 1, between some of the elements therein.

The mask 120 influences the manner in which the incoming light LS from the scene is projected onto the image sensor 130. Specifically, we assume that a basic optical system including the lens structure 111; 112 and the image sensor has a basic optical transfer function. The mask 120 is adapted to alter this basic optical transfer function into an enhanced optical transfer function, which is substantially less sensitive to variations A of an unknown distance R between the optical system 110 and the at least one subject 100 than the basic optical transfer function.

In other words, by including the mask 120 into the optical system 110 the proposed system's operating range is extended. For example, in a typical eye-tracking application wherein the distance R lies in the order of 60 cm, the operating range may extend over a range of distances $\Delta$ of approximately 80 cm, such that the eyes 101 and 102 may be located anywhere within 20 cm to 100 cm from the optical system 110.

Nevertheless, since the primary data $D_s$ registered by the image sensor 130 as such does not represent image contents in focus, the primary data $D_s$ must be post-processed to achieve the above-mentioned improvement of the operating range. Therefore, the processing unit 140 is adapted to receive the primary data $D_s$, and process this data such that resulting eye-tracking data $D_{EYE}$ is produced which represents a position estimate of the at least one eye 101; 102 and/or a gaze direction for the at least one eye 101; 102.

For efficiency reasons, it is desirable if the processing unit 140 is adapted to match the primary data $D_s$ against a target shape representing a typical eye shape, which has been transformed by the optical transfer function. Thereby, an earliest possible selection of relevant data can be made, i.e. essentially before the unit 140 performs any other processing. It is especially preferable, if the processing unit 140 is adapted to select a fraction of the primary data $D_s$, which represents a respective ROI (region of interest) on the sensor surface around each set of sensor elements that has a correlation with the target shape above a match threshold level.

Provided that a sensor surface of the image sensor 130 has a physical sensor element density, a basic resolution level is given by the number of sensor elements onto which the basic optical transfer function projects an in-focus light ray reflected from an object in the recorded scene.

According to one preferred embodiment of the invention, however, the enhanced optical transfer function is adapted to project light reflected from a single point in the scene onto a relatively large number of the image sensor's 130 sensor elements. This renders it possible to emulate a higher resolution level than what is given by the basic optical transfer function and the physical sensor element density. Namely, the processing unit 140 is adapted to process the primary data $D_s$ such that the eye-tracking data $D_{EYE}$ is derived at a precision, which is superior to a maximum precision attainable if the processing had been exclusively based on primary data $D_s$ at the basic resolution level of a traditional in-focus optical system.

Below, we will elaborate on the reasoning behind this. In a classic optical system a small piece of an object in focus is imaged at a small "single" point on the image sensor. According to the present invention, however, the proposed mask modifies the optical transfer function to be less sensitive to variations in distance to the objects being imaged, than that of a classic imaging system (i.e. given by the basic optical transfer function). The proposed enhanced optical transfer function is adapted to image a small piece of an object onto an area of the sensor surface which is larger than the area of the corresponding image area in a classic imaging system. For example, the enhanced optical transfer function may spread the image of one point of an object onto several sensor elements of the image sensor's 130 sensor area, whereas the basic optical transfer function projects this point onto a single sensor element.

In the classic optical system it is sometimes problematic to determine the exact position of small objects, for example a glint reflected in the cornea of an eye. Typically, such a glint is imaged onto one, or very few pixels. The size of the imaged object, in this case a glint, thus ultimately restricts how well the center of mass of the object may be determined. Particularly when determining the center of mass of small-object images, the result is largely dependant upon pixel response variations, fill factor less than 100% and the risk of hitting a defective sensor element (i.e. a "dead pixel"). In eye tracking applications such fluctuations may severely degrade the system's performance. Namely, for a typical operating distance, an eye tracker that repeatedly misplaces a glint by one pixel may easily induce an error of several centimeters with respect to an estimated gaze position, for instance on a computer screen. Naturally, this is not acceptable.

As mentioned above, according to one preferred embodiment of the invention, the enhanced optical transfer function is adapted to spread the image from one point in space onto more than one sensor element on the sensor surface. Hence, in the case of a glint reflected in the cornea of an eye, a point in space where the glint is located is projected in the form of a pattern covering multiple sensor elements on the image sensor's 130 sensor surface. This means that a mathematical pattern of an ideal glint passing through the enhanced optical transfer function can be aligned to the data from the image sensor in order to find a best pattern match. Since the pattern of an ideal glint passing through the enhanced optical transfer function is not a discrete pattern, however a continuous function, it is always mathematically possible to determine a more accurate position of a small glint than what is possible in images captured in focus of a classic imaging system. Therefore, the design strategy according to the invention is also less sensitive to the above-mentioned pixel response variations, fill factors less than 100% and the risk of having "dead pixels".

Additionally, the fact that the optical transfer function is continuous function (i.e. not a discrete pattern) may be used the other way around. Information, which in a classic in-focus imaging system would not be registered, or "hidden between pixels" (because the corresponding light rays were focused between two sensor elements), may according to one preferred embodiment of the invention be registered. To accomplish this, the alignment of the enhanced optical transfer function and the primary data $D_s$ registered by the image sensor 130 can be varied. Due to the sensor element density, it is physically necessary that the primary data $D_s$ is sampled at full pixel intervals. However, the enhanced optical transfer function must not be aligned with a particular sensor element/pixel position, or even a particular sub-pixel position. Instead, the origin of this function may be placed at any position in each respective dimension, X and Y. for instance at X=0.345. If so, the enhanced optical transfer function will be sampled at X=0.345, X=1.345, X=2.345, and so on. Of course, the same holds true also for the Y direction. This renders it possible to produce a classic image of a glint at many times higher resolution than what is supported by the image sensor's 130 sensor element density if used in a classic in-focus design. The resolution improvement is simply accomplished by sampling the enhanced optical transfer function at sub-pixel intervals. The same concept can be used when designing the algorithms, which extract the eye tracking data from the primary data $D_s$. The concept can be used to achieve high accuracy eye tracking data $D_{EYE}$, however not necessarily by creating a classic image as a step.

Naturally, the above-described quality improvements are applicable to all kinds of eye-tracking principles, i.e. DP-PCCR tracking, BP-PCCR tracking as well as any combinations thereof.

Figure 7A:
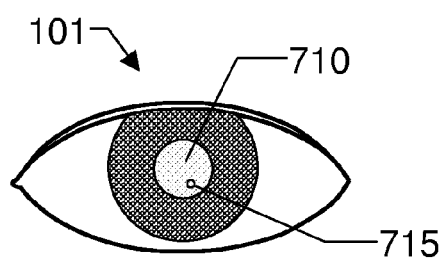
FIGS. 7a-c illustrate how bright- and dark-pupil images may be employed according to the first and second embodiments of the invention to determine a basis for a position estimate for a subject's eye.
Figure 7B:
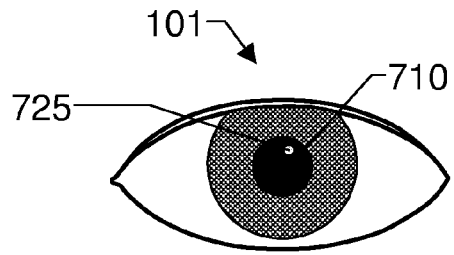
Figure 7C:
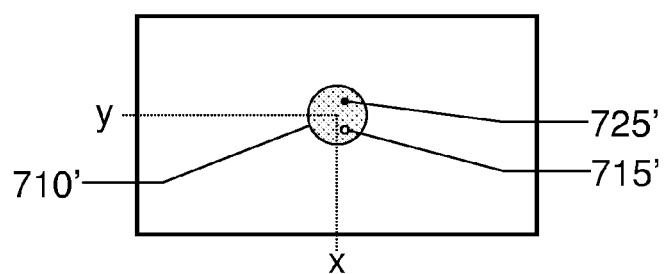

Turning now briefly to FIG. 7c, we see a schematic representation of a pupil having a position in the scene, which is given by a pair of coordinates x, y. According to one preferred embodiment of the invention, the processing unit 140 is adapted to initially determine at least one position candidate for the at least one of the eyes 101 and 102, i.e. rough x and y estimates.

Then, after having determined a set of position candidates x, y, the processing unit 140 is adapted to match different data sub-sets of the primary data $D_s$ representing each of the position candidates x, y against an eye model describing an ideal eye shape, which has been transformed by the optical transfer function. As a result, a set of correlation test values is obtained. Thereafter, based on the correlation test values, the processing unit is adapted to select at least one position candidate from the set of position candidates to represent at least one eye, for instance by means of a threshold level.

FIG. 2 shows an overview of a system according to one embodiment of the invention, and FIG. 3 illustrates further details of how a subject 100 and his/her eyes 101 and 102 may be illuminated according to this embodiment.

In addition to the units 110 and 140 described above with reference to the FIG. 1, the system includes at least one first light source L1 and at least one second light source L2a and L2b respectively. Each of the at least one first light source L1 is arranged relatively proximate to an optical axis $A_C$ of the optical system 110. Moreover, the light source(s) L1 is(are) oriented such that a respective main light beam B1 emitted there from essentially coincides with the optical axis Ac.

Thus, the light beam B1 is adapted to cause a bright-pupil effect with respect to images registered by a camera in which the optical system 110 is integrated.

Figure 4:
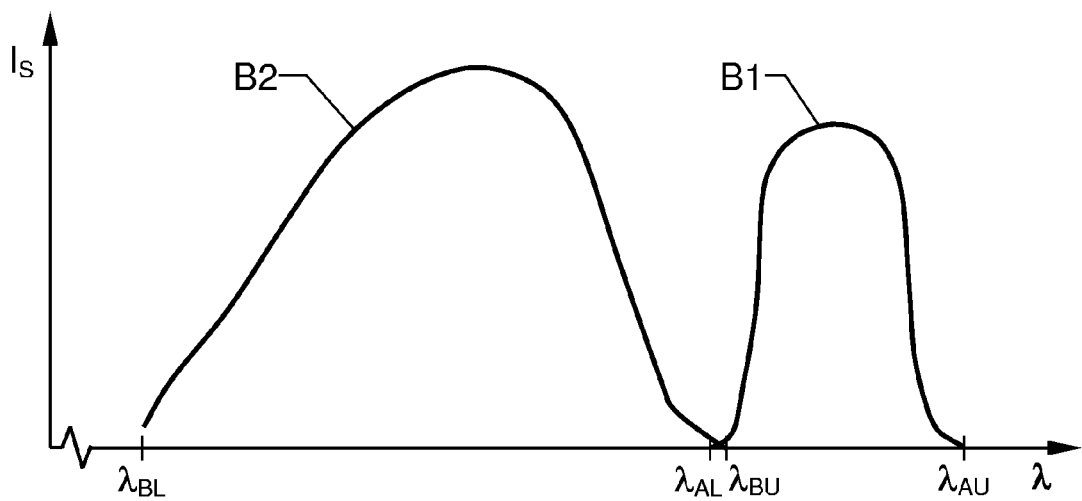
FIG. 4 is a diagram illustrating the relationship between two wavelength ranges used according to embodiments of the invention.

FIG. 4 shows a diagram, which represents a wavelength λ along the horizontal axis and a spectral intensity $I_S$ along the vertical axis. The light energy from the at least one first light source L1 is predominantly distributed within a first wavelength range $\lambda_{AL}$-$\lambda_{AU}$. According to the invention, essentially any visible or invisible light is conceivable here. However the first wavelength range preferably extends between a lower $\lambda_{AL}$ wavelength around 900 nm to 950 nm and an upper wavelength $\lambda_{AU}$ around 1000 nm.

Each of the at least one second light source L2a and L2b is adapted to emit light predominantly within a second wavelength range $\lambda_{BL}$-$\lambda_{BU}$ towards the subject 100. Contrary to the at least one first light source L1, each of the at least one second light source L2a and L2b is arranged at a distance dL2 from the optical axis Ac of the imaging device 110, such that a respective main light beam B2 emitted there from is positioned off-axis with respect to this optical axis Ac. Thus, the light beam B2 is adapted to cause a dark-pupil effect with respect to images registered by the camera in which the optical system 110 is integrated.

Given the above-specified $\lambda_{AL}$ and $\lambda_{AU}$ values, the second wavelength range preferably extends between a lower wavelength $\lambda_{BL}$ around 400 nm to 800 nm and an upper wavelength $\lambda_{BU}$ around 800 nm to 950 nm. In any case, the second wavelength range $\lambda_{BL}$ to $\lambda_{BU}$ is essentially separated from the first wavelength range $\lambda_{AL}$ to $\lambda_{AU}$. This means that a minor overlap of the ranges is acceptable, such as illustrated in the diagram.

Figure 5:
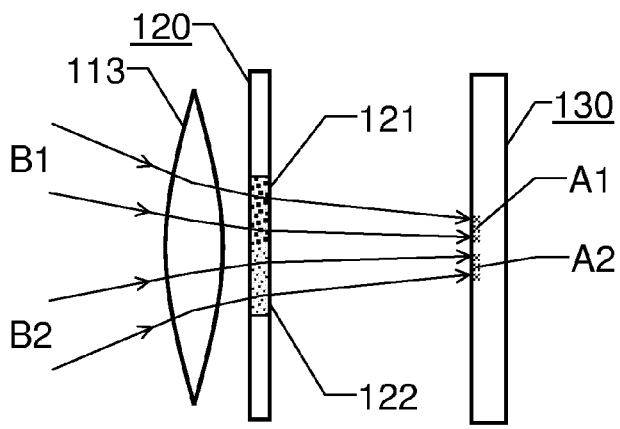
FIG. 5 illustrates the working principle of a mask according to a first embodiment of the invention.

FIG. 5 illustrates how a mask 120 according to a first embodiment of the invention may be used to benefit from the above-mentioned bright- and dark-pupil effects accomplished by the at least one first light source L1 and the at least one second light source L2a and L2b respectively in the processing performed by the proposed processing device 140.

In this example, the mask 120 and a lens 113 are adapted to realize a first optical transfer function with respect to light within the first wavelength range $\lambda_{AL}$-$\lambda_{AU}$, and realize a second optical transfer function with respect to light within the second wavelength range $\lambda_{BL}$-$\lambda_{BU}$. As a result, light within the first wavelength range $\lambda_{AL}$-$\lambda_{AU}$ is directed towards a first area A1 on a sensor surface of the image sensor 130, and direct light within the second wavelength range $\lambda_{BL}$-$\lambda_{BU}$ is directed towards a second area A2 on the sensor surface.

For reasons of a clear presentation the first and second optical transfer functions are here symbolized by two separate volumes 121 and 122 respectively in the mask 120. In practice, however, these volumes may very well occupy one and the same space in the mask 120.

Moreover, the first and second areas A1 and A2 may either be physically separated from one another (as shown in the FIG. 5), or these areas may overlap more or less. Provided that the first and second optical transfer functions represent orthogonal bases, the areas A1 and A2 may overlap one another entirely.

The processing unit 140 is adapted to produce a bright-pupil eye-tracking parameter based on a first sub-set of the primary data $D_s$, which has been registered by sensor elements within the first area A1. Analogously, the processing unit 140 is adapted to produce a dark-pupil eye-tracking parameter based on a second sub-set of the primary data $D_s$, which has been registered by sensor elements within the second area A2.

Figure 6:
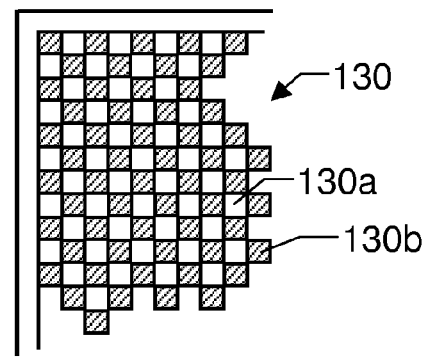
FIG. 6 illustrates a configuration of a sensor area of an image sensor according to a second embodiment of the invention.

FIG. 6 illustrates how a sensor area of an image sensor 130 is configured according to a second embodiment of the invention. Also in this embodiment, the design is intended to enable the processing performed by the processing device 140 to benefit from the bright- and dark-pupil effects accomplished by the at least one first light source L1 and the at least one second light source L2a and L2b respectively.

Here, however, the sensor 130 has two types of sensor elements, namely a first set of elements 130a wherein each element (symbolized by means of a white square) is adapted to detect light within the first wavelength range $\lambda_{AL}$-$\lambda_{AU}$, and a second set of sensor elements 130b wherein each element (symbolized by means of a dark square) is adapted to detect light within the second wavelength range $\lambda_{BL}$-$\lambda_{BU}$. Thus, the first set of sensor elements 130a register a first sub-set of the primary data $D_s$ representing bright-pupil information, and the second set of sensor elements 130b register a second sub-set of the primary data $D_s$ representing dark-pupil information.

According to one preferred embodiment of the invention, the light detecting area of the image sensor 115 is configured such that each element in the first set of sensor elements 130a adjoins at least one element in the second set of sensor elements 130b. Consequently, as a special case of this embodiment, the elements in the first and second sets of sensor elements 130a and 130b can be arranged in a checkered pattern, as illustrated in the FIG. 6.

In any case, the processing unit 140 is adapted to produce a bright-pupil eye-tracking parameter based on the first sub-set of the primary data $D_s$, and produce a dark-pupil eye-tracking parameter based on the second sub-set of the primary data $D_s$.

In order to further illustrate how bright- and dark-pupil images may be employed according to the first and second embodiments of the invention to determine a basis for a position x, y estimate for a subject's eye, we now refer to FIGS. 7a, b and c.

The FIG. 7a shows an eye 101 having a bright pupil 710. Here, the eye's 101 pupil 710 appears relatively bright due to a strong retinal reflection of the at least one first light source L1. One or more glints 715 resulting from the at least one light source Li may also be present.

The FIG. 7b shows another eye, which has a pupil 710 that appears dark in the absence of a retinal reflection. However, one or more glints 725 resulting from the at least one second light source L2a and L2b may be present.

Since the primary data $D_s$ registered by the image sensor 130 is not in focus, none of the images in the FIG. 7a or 7b as such are registered here. Nevertheless, the primary data $D_s$ contains equivalent information, which is separable into a first and a second sub-set as described above (i.e. representing bright- and dark-pupil eye-tracking parameters respectively). Therefore, according to one preferred embodiment of the invention, the processing unit 140 is adapted to produce the eye-tracking data $D_{EYE}$ based on both the bright- and dark-pupil eye-tracking parameters. The FIG. 7c illustrates this by means of a composite image representing a subtraction of the image content represented by the dark-pupil image in the FIG. 7b from the image content represented by the bright-pupil image in the FIG. 7a. Hence, the composite image includes glint data 715' from the first sub-set of the primary data $D_s$ as well as glint data 725' from the second sub-set of the primary data $D_s$. Of course, the composite image in the FIG. 7c need only exist as an abstract representation in the processing unit 140 (i.e. not as an actual image) in order to render it possible to determine position estimate x, y for the eye 101.

Figure 8:
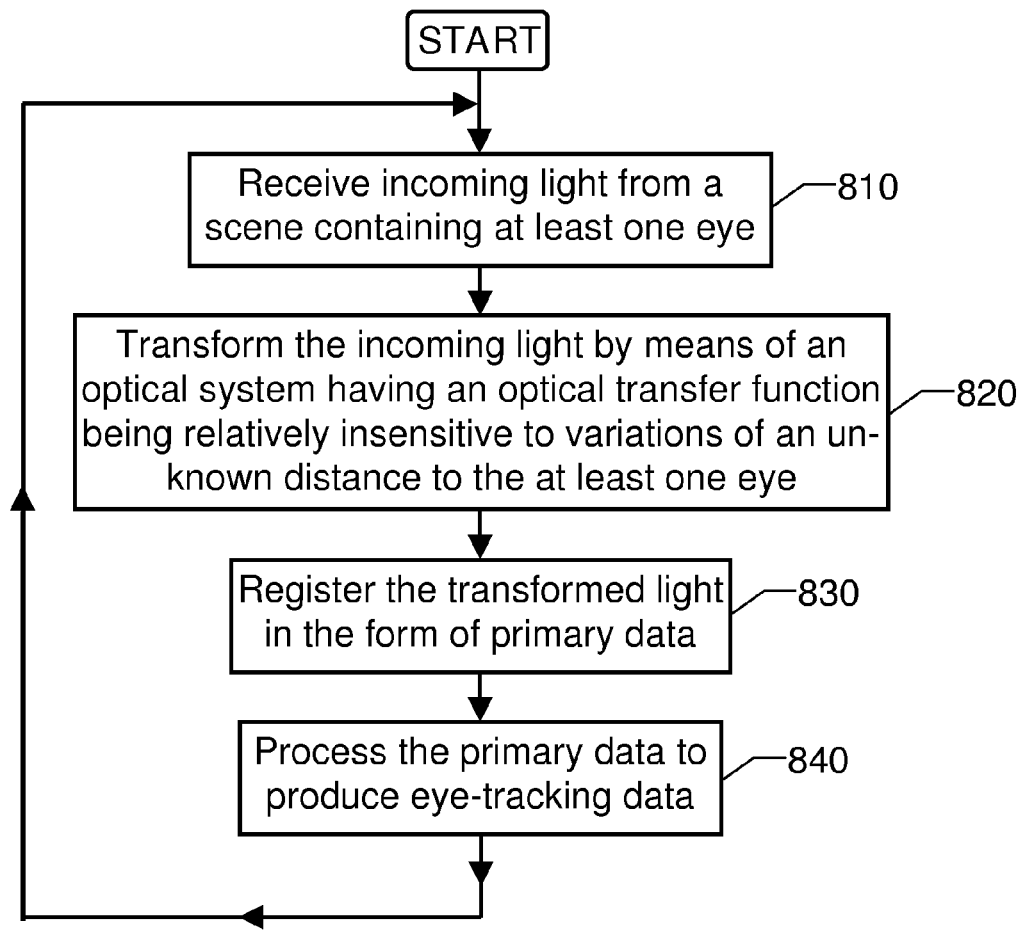
FIG. 8 illustrates, by means of a flow diagram, a general method according to the invention.

To sum up, the general method according to the invention for automatically registering and tracking at least one eye of at least one subject will now be described with reference to the flow diagram in FIG. 8.

An initial step 810 receives incoming light from a scene containing the at least one subject, and thus presumably the at least one eye too. Then, a step 820 transforms the incoming light by means of an optical system having an enhanced optical transfer function, which is substantially less sensitive to variations of an unknown distance between the proposed optical system and the at least one subject than a basic optical transfer function of an equivalent optical system. Specifically, the proposed optical system includes a lens structure and a mask, wherein the mask is adapted to alter the basic optical transfer function into the enhanced optical transfer function as described above.

After having passed the optical system a step 830 registers the spatially distributed transformed light by means of an image sensor, and thus accomplishes primary data $D_s$.

Subsequently, a step 840 processes the primary data $D_s$ to produce resulting eye-tracking data $D_{EYE}$. This data, in turn, represents a position estimate of the at least one eye and/or a gaze direction for the at least one eye.

All of the process steps, as well as any sub-sequence of steps, described with reference to the FIG. 8 above may be controlled by means of a programmed computer apparatus. Moreover, although the embodiments of the invention described above with reference to the drawings comprise computer apparatus and processes performed in computer apparatus, the invention thus also extends to computer programs, particularly computer programs on or in a carrier, adapted for putting the invention into practice. The program may be in the form of source code, object code, a code intermediate source and object code such as in partially compiled form, or in any other form suitable for use in the implementation of the process according to the invention. The program may either be a part of an operating system, or be a separate application. The carrier may be any entity or device capable of carrying the program. For example, the carrier may comprise a storage medium, such as a Flash memory, a ROM (Read Only Memory), for example a DVD (Digital Versatile/Video Disc), a CD (Compact Disc) or a semiconductor ROM, an EPROM (Erasable Programmable Read-Only Memory), an EEPROM (Electrically Erasable Programmable Read-Only Memory), or a magnetic recording medium, for example a floppy disc or hard disc. Further, the carrier may be a transmissible carrier such as an electrical or optical signal which may be conveyed via electrical or optical cable or by radio or by other means. When the program is embodied in a signal which may be conveyed directly by a cable or other device or means, the carrier may be constituted by such cable or device or means. Alternatively, the carrier may be an integrated circuit in which the program is embedded, the integrated circuit being adapted for performing, or for use in the performance of, the relevant processes.

The term "comprises/comprising" when used in this specification is taken to specify the presence of stated features, integers, steps or components. However, the term does not preclude the presence or addition of one or more additional features, integers, steps or components or groups thereof.

The reference to any prior art in this specification is not, and should not be taken as an acknowledgement or any suggestion that the referenced prior art forms part of the common general knowledge in Australia.

The invention is not restricted to the described embodiments in the figures, but may be varied freely within the scope of the claims.

The invention claimed is:

1. A system for automatically registering and tracking at least one eye of at least one subject, comprising:
    an optical system including an image sensor configured to register spatially distributed light and produce resulting primary data, and a lens structure configured to receive incoming light reflected from a scene containing the at least one subject and direct at least a portion of the incoming light towards the image sensor, the optical system having a basic optical transfer function by the image of a given piece of an object being projected onto an area of the image sensor, which is larger than a corresponding area in a classic imaging system;
    a processing unit configured to derive eye-tracking data based on the primary data, and
    wherein the optical system further comprises a mask which is arranged between the at least one subject and the image sensor, the mask is configured to alter the basic optical transfer function into an enhanced optical transfer function which is configured to spread an image from one point in space onto more than one sensor element on a sensor surface of the image sensor, and the enhanced optical transfer function is substantially less sensitive to variations of an unknown distance between the optical system and the at least one subject than the basic optical transfer function, and the processing unit is configured to receive the primary data and process the primary data to produce resulting eye-tracking data representing at least one of a position estimate of the at least one eye and a gaze direction for the at least one eye.

2. The system according to claim 1, wherein the image sensor is configured to exclusively transfer a high-relevance fraction of the primary data to the processing unit, the high-relevance fraction being selected by the processing unit based on at least one of previously derived eye-tracking data and data registered by one or more auxiliary sensors connected to the system.

3. The system according to claim 1, wherein the enhanced optical transfer function is configured to project light reflected from a single point in the scene onto a number of sensor elements of a sensor surface in the image sensor thus emulating a higher resolution level than a basic resolution level given by the basic optical transfer function and a physical sensor element density of the sensor surface, and
    wherein the processing unit is configured to process the primary data such that the eye-tracking data is derived at a precision being superior to a maximum precision attainable exclusively based on eye-tracking data derived from primary data at the basic resolution level of a classic in-focus optical system.

4. The system according to claim 1, wherein the processing unit is configured to match the primary data against a target shape representing a typical eye shape transformed by the optical transfer function.

5. The system according to claim 4, wherein the processing unit is configured to select a fraction of the primary data representing a respective region of interest on the sensor surface around each set of sensor elements having a correlation with the target shape above a match threshold level.

6. The system according to claim 1, wherein the processing unit is configured to determine at least one position candidate for the at least one eye, and after having determined a set of position candidates, the processing unit is configured to match data sub-sets of the primary data representing each of the position candidates against an eye model representing an ideal eye shape transformed by the optical transfer function to obtain a set of correlation test values, and select, based on the correlation test values, at least one position candidate from the set of position candidates to represent at least one eye.

7. The system according to claim 1, wherein the system comprises:
at least one first light source arranged relatively proximate to an optical axis of the optical system, the at least one first light source being oriented such that a main light beam emitted there from essentially coincides with the optical axis, the light energy from the at least one first light source being predominantly distributed within a first wavelength range; and
at least one second light source configured to emit light predominantly within a second wavelength range towards the at least one subject, the second wavelength range being essentially separated from the first wavelength range, and the at least one second light source being arranged at a distance from the optical axis of the imaging device such that a main light beam emitted there from is positioned off-axis with respect to this optical axis.

8. The system according to claim 7, wherein the mask is configured to realize a first optical transfer function with respect to light within the first wavelength range and direct light within this range to a first area on a sensor surface of the image sensor, and realize a second optical transfer function with respect to light within the second wavelength range and direct light within this range to a second area on the sensor surface, and
wherein the processing unit is configured to produce at least one of a bright-pupil eye-tracking parameter based on a first subset of the primary data registered by sensor elements within the first area, and a dark-pupil eye-tracking parameter based on a second sub-set of the primary data registered by sensor elements within the second area.

9. The system according to claim 7, wherein the image sensor comprises:
a first set of sensor elements wherein each element is configured to detect light within the first wavelength range;
a second set of sensor elements wherein each element is configured to detect light within the second wavelength range; and
wherein the processing unit is configured to produce a bright-pupil eye-tracking parameter based on a first subset of the primary data registered by the first set of sensor elements, and produce a dark-pupil eye-tracking parameter based on a second sub-set of the primary data registered by the second set of sensor elements.

10. The system according to claim 9, wherein each element in the first set of sensor elements adjoins at least one element in the second set of sensor elements.

11. The system according to claim 10, wherein the elements in the first and second sets of sensor elements are arranged in a checkered pattern.

12. The system according to claim 10, wherein the enhanced optical transfer function is configured to project light reflected from a single point in the scene onto a number of the elements in the first and second sets of sensor elements thus emulating a higher resolution level than a basic resolution level given by the basic optical transfer function and a physical sensor element density of the sensor surface; and
wherein the processing unit is configured to process the primary data such that the eye-tracking data is derived at a precision being superior to a maximum precision attainable exclusively based on eye-tracking data derived from primary data at the basic resolution level of a classic in-focus optical system.

13. The system according to claim 8, wherein the processing unit is configured to produce the eye-tracking data based on at least one of the bright and dark pupil eye-tracking parameters.

14. A method of automatically registering and tracking at least one eye of at least one subject, wherein primary data representing spatially distributed light is registered, the light having been transmitted from a scene containing the at least one subject via an optical system comprising a lens structure and a mask to an image sensor, the mask being configured to alter a basic optical transfer function of the lens structure and the image sensor into an enhanced optical transfer function which is substantially less sensitive to variations of an unknown distance between the optical system and the at least one subject than the basic optical transfer function by the image of a given piece of an object being projected onto an area of the image sensor, which is larger than a corresponding area in a classic imaging system, and the method comprising:
receiving the primary data; and
processing the primary data to produce resulting eye-tracking data which represents at least one of a position estimate of the at least one eye and a gaze direction for the at least one eye.

15. The method according to claim 14, wherein processing the primary data comprises exclusively processing a high-relevance fraction of the primary data to produce the eye-tracking data, and the method further comprising:
selecting the high-relevance fraction based on at least one of previously derived eye-tracking data and data registered by one or more auxiliary sensors.

16. The method according to claim 14, wherein the enhanced optical transfer function being configured to project light reflected from a single point in the scene onto a number of sensor elements of a sensor surface in the image sensor thus emulating a higher resolution level than a basic resolution level given by the basic optical transfer function and a physical sensor element density of the sensor surface, and the method further comprising:
processing the primary data such that the eye-tracking data is derived at a precision being superior to a maximum precision attainable exclusively based on eye-tracking data derived from primary data at the basic resolution level of a classic in-focus optical system.

17. The method according to claim 14, further comprising:
matching the primary data against a target shape representing a typical eye shape transformed by the optical transfer function.

18. The method according to claim 17, further comprising:
selecting a fraction of the primary data to represent a respective region of interest for each sub-set of the primary data which has a correlation with the target shape above a match threshold level.

19. The method according to claim 14, further comprising:
determining at least one position candidate for the at least one eye, thereafter;
matching, for each of the at least one position candidate, a respective data sub-set of the primary data representing the position candidate against an eye model representing an ideal eye shape transformed by the optical transfer function to obtain a respective correlation test value; and
selecting, based on the correlation test values, at least one position candidate from the set of position candidates to represent at least one eye.

20. The method according to claim 14, further comprising :
  illuminating the scene by means of at least one first light source arranged relatively proximate to an optical axis of the optical system, the at least one first light source being oriented such that a main light beam emitted there from essentially coincides with the optical axis, the at least one first light source emitting light energy predominantly within a first wavelength range; and
  illuminating the scene by means of at least one second light source arranged at a distance from the optical axis of the imaging device such that a main light beam emitted there from is positioned off-axis with respect to this optical axis, the at least one second light source emitting light predominantly within a second wavelength range which is essentially separated from the first wavelength range.

21. The method according to claim 20, wherein the mask being configured to transform the incoming light from the scene such that light within the first wavelength range is directed towards a first area on a sensor surface, and light within the second wavelength range is directed towards a second area on the sensor surface, and the method further comprising:
  producing at least one of a bright-pupil eye-tracking parameter based on a sub-set of the primary data registered by sensor elements within the first area, and a dark-pupil eye-tracking parameter based on a sub-set of the primary data registered by sensor elements within the second area.

22. The method according to claim 21, wherein producing the eye-tracking data is based on at least one of the bright and dark pupil eye-tracking parameters.

23. A computer program directly loadable into the internal memory of a computer, comprising software for controlling the processes of claim 14 when said program is run on the computer.

24. A computer readable medium, having a program recorded thereon, where the program is to make a computer control the processes of claim 14.

* * * * *